United States Patent
Baillet et al.

(10) Patent No.: US 10,894,133 B2
(45) Date of Patent: Jan. 19, 2021

(54) DEVICE FOR DISPENSING A FLUID PRODUCT

(71) Applicant: APTAR FRANCE SAS, Le Neubourg (FR)

(72) Inventors: Matthieu Baillet, Rouen (FR); Dolorès Carballo, Montreal (CA); Hélène Dulude, Montreal (CA); Franck Poullain, La Haye Malherbe (FR)

(73) Assignee: APTAR FRANCE SAS, Le Neubourg (FR)

( * ) Notice: Subject to any disclaimer, the term of this patent is extended or adjusted under 35 U.S.C. 154(b) by 209 days.

(21) Appl. No.: 16/304,025

(22) PCT Filed: Jun. 8, 2017

(86) PCT No.: PCT/FR2017/051448
§ 371 (c)(1),
(2) Date: Nov. 21, 2018

(87) PCT Pub. No.: WO2017/220880
PCT Pub. Date: Dec. 28, 2017

(65) Prior Publication Data
US 2020/0316318 A1    Oct. 8, 2020

(30) Foreign Application Priority Data

Jun. 20, 2016   (FR) ..................................... 16 55706

(51) Int. Cl.
*A61M 11/02*   (2006.01)
*B05B 11/06*   (2006.01)
(Continued)

(52) U.S. Cl.
CPC ........ *A61M 11/02* (2013.01); *A61M 15/0028* (2013.01); *A61M 15/0061* (2014.02);
(Continued)

(58) Field of Classification Search
CPC .............. A61M 11/02; A61M 15/0061; A61M 15/0028; A61M 15/08; B05B 11/062; B05B 11/3053; B05B 11/02; B05B 12/002
See application file for complete search history.

(56) References Cited

U.S. PATENT DOCUMENTS

| 6,398,074 B1 * | 6/2002 | Bruna | A61M 15/0036 |
| | | | 222/82 |
| 6,401,987 B1 * | 6/2002 | Oechsel | B05B 11/02 |
| | | | 222/321.7 |

(Continued)

FOREIGN PATENT DOCUMENTS

| FR | 3 007 992 A1 | 1/2015 |
| WO | 99/046055 A1 | 9/1999 |

(Continued)

OTHER PUBLICATIONS

International Search Report for PCT/FR2017/051448 dated Sep. 15, 2017 [PCT/ISA/210].

(Continued)

*Primary Examiner* — Jeremy Carroll
(74) *Attorney, Agent, or Firm* — Sughrue Mion, PLLC

(57) ABSTRACT

A dispenser device for dispensing a fluid or powder composition, the dispenser device comprising: a dispenser head (1) that is provided with a dispenser outlet (10) that is formed at the end of a hollow sleeve (3); an air expeller (20) for generating a flow of air while the device is being actuated, said air expeller including a piston (21) that slides in an air chamber (22) between a rest position and a dispensing position, said air chamber (22) including a cylindrical body in which said piston (21) slides in airtight manner; and a reservoir (30) that contains a single dose of composition, said reservoir (30) including an air inlet (31)

(Continued)

Figure 1A:
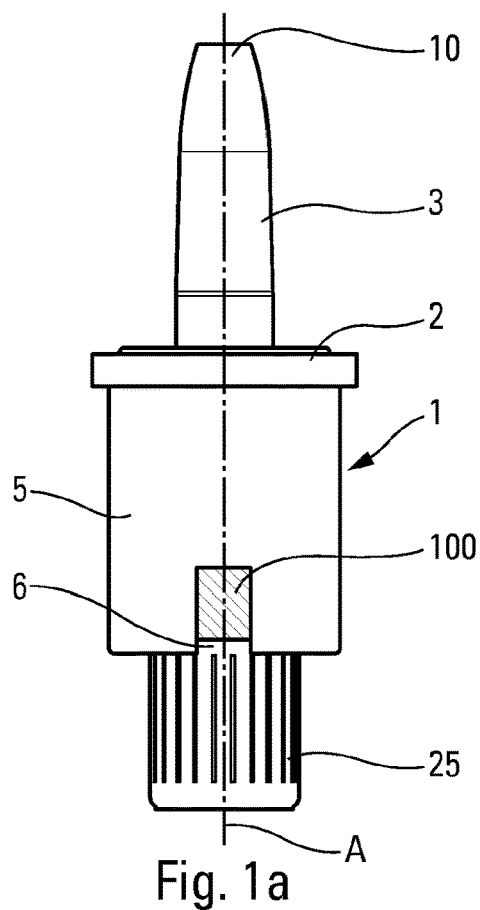

that is connected to said air expeller (20), and a composition outlet (32) that is connected to said dispenser outlet (10), said air inlet (31) including a composition retainer member (40) for retaining the composition in the reservoir (30) until the composition is dispensed, and said composition outlet (32) being closed by a closure element (50) that is force fitted in the composition outlet (32) of the reservoir (30); said device further comprising a mechanical opening system (61, 62) that co-operates with said closure element (50) so as to expel it mechanically from its closed position while the device is being actuated; said device further comprising an indicator (100; 50) that, in the rest position before actuation, is in a first state, and that after actuation passes into a second state, the passage from the first to the second state informing the user that the device has been actuated, said first state being a visible state and said second state being a non-visible state, said device including a pusher element (25) that is secured to said piston (21), and on which the user presses during actuation, said dispenser head (1) including a skirt (5) that is arranged around said air chamber (22), said pusher element (25), in its rest position before actuation, projecting axially out from said skirt (5), and after actuation, being arranged inside said skirt (5), said pusher element (25) including an indicator (100) that is visible before actuation and that is not visible after actuation.

2 Claims, 2 Drawing Sheets

(51) Int. Cl.
*B05B 11/00* (2006.01)
*A61M 15/08* (2006.01)
*A61M 15/00* (2006.01)
*B05B 11/02* (2006.01)

(52) U.S. Cl.
CPC ............. *A61M 15/08* (2013.01); *B05B 11/02* (2013.01); *B05B 11/062* (2013.01); *B05B 11/3053* (2013.01); *A61M 2202/04* (2013.01); *A61M 2202/064* (2013.01); *A61M 2205/073* (2013.01); *A61M 2205/584* (2013.01)

(56) References Cited

U.S. PATENT DOCUMENTS

| | | | | |
|---|---|---|---|---|
| 6,446,839 | B1* | 9/2002 | Ritsche | A61M 5/3158 222/153.13 |
| 6,866,039 | B1* | 3/2005 | Wright | A61M 15/0041 128/203.15 |
| 6,877,672 | B2* | 4/2005 | Stihl | A61M 15/0028 222/82 |
| 2016/0082455 | A1* | 3/2016 | Baillet | A61M 11/02 222/216 |
| 2016/0167071 | A1* | 6/2016 | Baillet | A61M 15/0028 222/23 |
| 2016/0296957 | A1* | 10/2016 | Baillet | A61M 15/0028 |

FOREIGN PATENT DOCUMENTS

| | | |
|---|---|---|
| WO | 02/045866 A1 | 6/2002 |
| WO | 2014/147329 A1 | 9/2014 |

OTHER PUBLICATIONS

International Preliminary Report on Patentability with Written Opinion dated Jan. 3, 2019, issued by the International Searching Authority in application No. PCT/FR2017/051448.

* cited by examiner

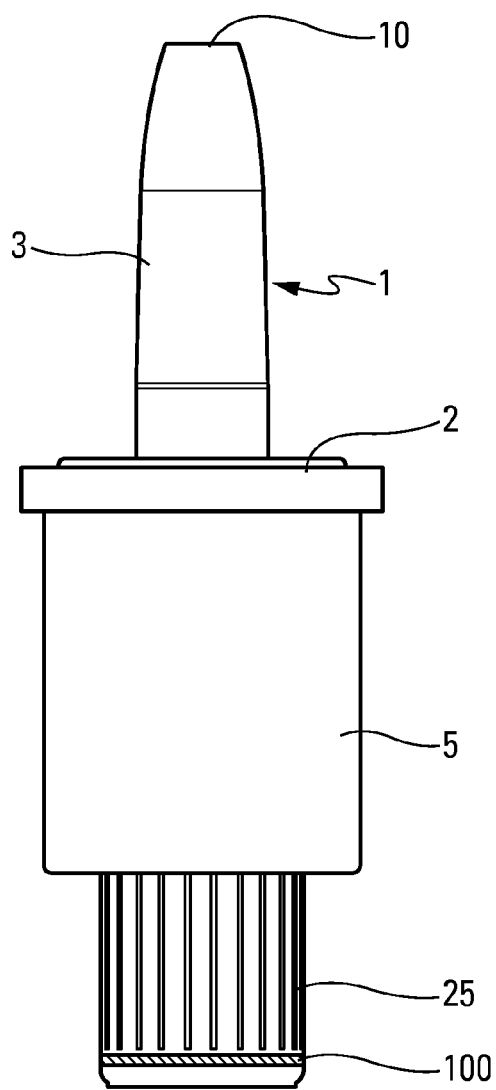
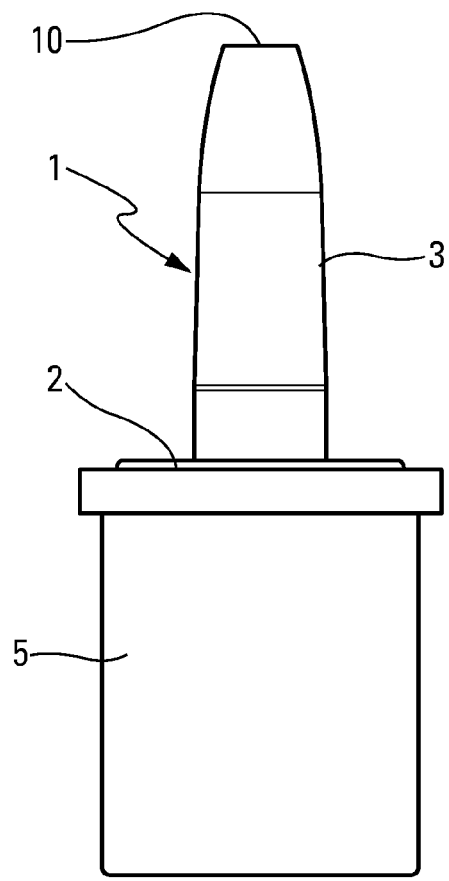
Fig. 3
Fig. 4

DEVICE FOR DISPENSING A FLUID PRODUCT

CROSS REFERENCE TO RELATED APPLICATIONS

This application is a National Stage of International Application No. PCT/FR2017/051448 filed Jun. 8, 2017, claiming priority based on Japanese Patent Application No. 1655706 filed Jun. 20, 2016.

The present invention relates to a dispenser device for dispensing a fluid or powder composition, and more particularly it relates to a device for dispensing a single dose of a composition contained in a reservoir, by means of a flow of air under pressure.

Documents WO 99/46055 and WO 02/45866 disclose devices of this type. A drawback of those devices is that it may be difficult, in particular for a novice user, to know whether or not the device has been used. The user may thus possess a device thinking that it contains a dose to be dispensed, while in reality it is empty.

Documents FR 3 007 992 and WO 2014/147329 describe other prior-art devices.

An object of the present invention is to provide a fluid or powder dispenser device that does not have the above-mentioned drawbacks.

Another object of the present invention is to provide such a fluid or powder dispenser device that gives clear information to the user, so as to enable the user to know whether or not the device has been actuated.

Another object of the present invention is to provide a fluid or powder dispenser device that is simple and inexpensive to manufacture and to assemble.

The present thus provides a dispenser device for dispensing a fluid or powder composition, the dispenser device comprising: a dispenser head that is provided with a dispenser outlet that is formed at the end of a hollow sleeve; an air expeller for generating a flow of air while the device is being actuated, said air expeller including a piston that slides in an air chamber between a rest position and a dispensing position, said air chamber including a cylindrical body in which said piston slides in airtight manner; and a reservoir that contains a single dose of composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir; said device further comprising a mechanical opening system that co-operates with said closure element so as to expel it mechanically from its closed position while the device is being actuated; said device further comprising an indicator that, in the rest position before actuation, is in a first state, and that after actuation passes into a second state, the passage from the first to the second state informing the user that the device has been actuated, said first state being a visible state and said second state being a non-visible state, said device including a pusher element that is secured to said piston, and on which the user presses during actuation, said dispenser head including a skirt that is arranged around said air chamber, said pusher element, in its rest position before actuation, projecting axially out from said skirt, and after actuation, being arranged inside said skirt, said pusher element including an indicator that is visible before actuation and that is not visible after actuation.

Advantageously, said indicator is formed by a colored strip that extends around said pusher element.

Figure 1B:
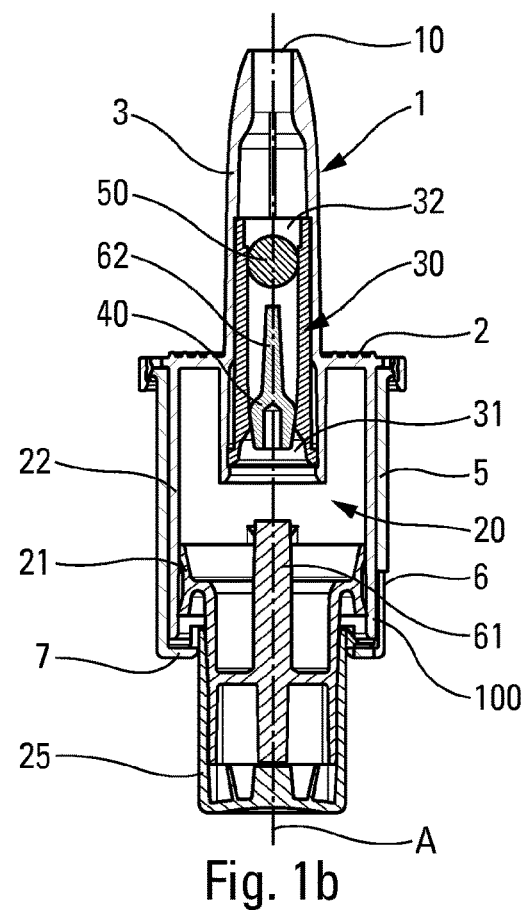
Figure 2A:
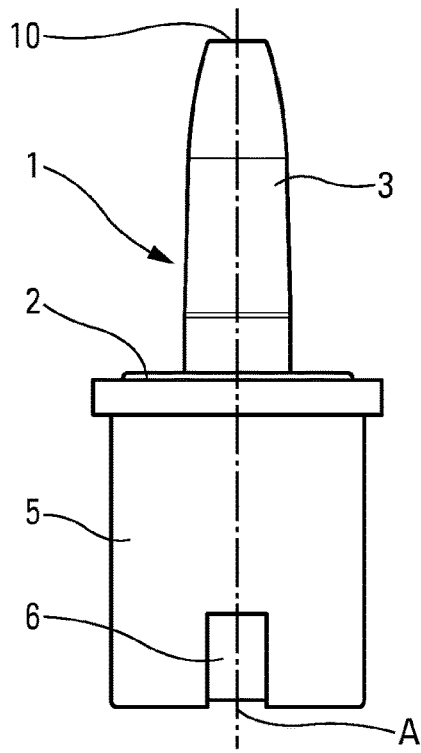
Figure 2B:
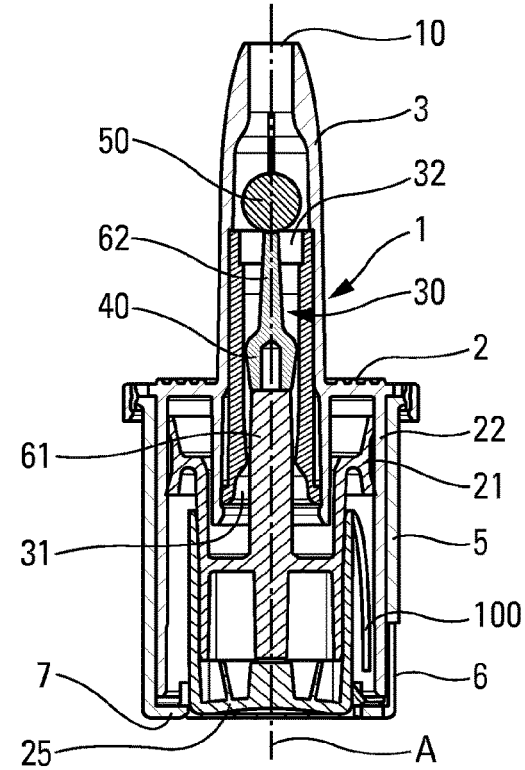

These characteristics and advantages, and others, appear more clearly from the following detailed description of several embodiments, given by way of non-limiting example, and with reference to the accompanying drawings, in which:

FIG. 1*a* is a diagrammatic side view of a fluid or powder dispenser device in an embodiment not covered by the present invention, shown in its rest position before actuation;

FIG. 1*b* is a diagrammatic section view similar to the view in FIG. 1*a*;

FIG. 2*a* is a diagrammatic side view of the FIG. 1*a* device, shown after actuation;

FIG. 2*b* is a diagrammatic section view similar to the view in FIG. 2*a*;

FIG. 3 is a diagrammatic side view of a fluid or powder dispenser device in an advantageous embodiment of the present invention, shown in its rest position before actuation; and FIG. 4 is a view similar to the view in FIG. 3, shown after actuation.

The present invention relates more particularly to a device of the type disclosed in document WO 02/45866. However, it should be understood that the present invention is not limited to that type of device, but, on the contrary, applies to any type of fluid or powder dispenser device of the single-dose type, i.e. including a reservoir that contains only a single dose that is dispensed in a single actuation.

In the description below, the terms "top", "bottom", "upwards", and "downwards" are relative to the upright position of the device shown in the figures. The terms "axial" and "radial" are relative to the longitudinal central axis A of the device, shown in FIGS. 1*a*, 1*b*, 2*a*, and 2*b*.

The device includes a reservoir 30 including an air inlet 31 and a composition outlet 32, and containing and single dose of fluid, liquid, or powder composition. The air inlet 31 of the reservoir is connected to an air expeller 20, and the composition outlet 32 of the reservoir is connected to a dispenser outlet 10 of the device. The composition outlet 32 is closed by a closure element 50 that is force fitted in said composition outlet 32. The air inlet 31 is provided with a composition retainer member 40 that is suitable for retaining the composition in the reservoir 30 before the device is actuated. The air expeller 20 is actuated manually by the user, and is suitable for creating a flow of air that passes through the reservoir 30 so as to deliver the composition that it contains towards the dispenser outlet 10.

The reservoir 30 is secured, in particular as a tight fit, in a dispenser head 1 that includes the dispenser outlet 10. Advantageously, the dispenser head 1 includes a finger rest 2 that extends radially so as to facilitate actuation. A hollow sleeve 3 extends axially upwards from said finger rest 2, and is terminated at said dispenser outlet 10. Preferably, the hollow sleeve 3 is of small radial dimension, so as to be suitable for inserting in a nostril at the time of actuation. On the opposite side of the finger rest 2, the dispenser head 1 includes a skirt 5 that extends axially downwards from said finger rest 2.

The device includes a mechanical opening system 61, 62 that is preferably secured to the air expeller 20, i.e. it is actuated simultaneously with said air expeller 20 being actuated, and that is suitable for co-operating with said closure element 50 so as to expel it mechanically from its closed position while the device is being actuated. In the embodiment shown in the figures, the mechanical opening system includes a set of rods 61, 62, having a first rod portion 61 that is secured to the air expeller 20, and a second rod portion 62 that is thrust by said first rod portion 61 when the device is actuated. At the end of their actuation stroke, i.e. in the dispensing position, the set of rods 61, 62 co-operate with the closure element 50 so as to expel it mechanically from its closed position.

The composition retainer member 40 may advantageously be made integrally with the second rod portion 62. Thus, the composition retainer member 40 can be made in leaktight and airtight manner before the device is actuated, the air pressure created by the air expeller 20 penetrating into the reservoir 30 only when said retainer member 40 is moved together with the second rod portion 62, by being thrust by the first rod portion 61.

The closure element 50 may be spherical, e.g. a ball made of plastics material, as shown in FIGS. 1b and 2b.

The air expeller 20 shown in FIGS. 1b and 2b includes a piston 21 that slides in an air chamber 22, the piston 21 being actuated manually by the user. The air chamber 22 may be formed by a hollow axial cylinder that is made integrally with the finger rest 2 of the dispenser head 1, the bottom side of said air chamber 22 being open, and being closed by said piston 21. Advantageously, the skirt 5 of the head is thus arranged around said air chamber 22, and in particular may be formed by a hollow cylinder that is fastened, e.g. snap-fastened, in the finger rest 2 of the dispenser head 1.

Advantageously, in order to protect the piston 21, the bottom edge of the skirt 5 surrounds the bottom edge of the air chamber 22, and includes a radial flange 7 that extends radially inwards below said bottom edge of the air chamber 22.

Advantageously, actuation of the device is performed by means of a pusher element 25 that is assembled on said piston 21.

The piston 21 is secured to the first rod portion 61, advantageously being formed integrally therewith.

When it is desired to actuate the device, the user firstly places fingers on the finger rest 2 of the dispenser head 1, and secondly a thumb on the pusher element 25, and exerts an axial actuation force that moves the first rod portion 61 and the piston 21 towards the dispensing position. The piston 21 of the air expeller co-operates in airtight manner with the air chamber 22, such that the air contained in said air chamber 22 is compressed progressively during actuation.

After an initial actuation stroke for compressing air, the top axial end of the first rod portion 61 comes into contact with the retainer member 40 and thus with the second rod portion 62.

Continued actuation moves said retainer member 40 axially upwards inside the reservoir 30, thus away from its position of sealed shutting or closing of the air inlet 32. At that moment, the compressed air in the air chamber 22 can thus penetrate into the reservoir 30. At the same moment, the top axial end of the second rod portion 62 comes into contact with the closure element 50.

Continued actuation thus moves the closure element 50 axially upwards, away from its closed position.

When the sealing of the closure element 50 is broken, said closure element is expelled out from the reservoir 30 so as to enable the fluid or powder to be dispensed under the effect of the compressed air. The closure element 50 thus becomes jammed in splines of the dispenser head 1, which splines prevent in particular any risk of said closure element being expelled out from said dispenser head 1. The dispensing position, at the end of the actuation stroke and after dispensing the composition, is shown in FIGS. 2a and 2b.

In the invention, the device includes an indicator that makes it possible to inform the user about the state of the device, namely before or after actuation. The indicator passes from a first state, in the rest position, before actuation, to a second state after actuation, the passage from the first to the second state informing the user that the device has been actuated.

In the invention, the indicator is clearly visible before actuation and disappears after actuation.

FIGS. 1a,b and 2a,b show an embodiment that is not covered by the present invention, but that describes the device as a whole in detailed manner.

FIGS. 3 and 4 show an advantageous embodiment of the present invention.

In this embodiment, the indicator 100 is formed on the outside of the pusher element 25.

Thus, in the rest position, before actuation, the pusher element 25 extends axially out from the skirt 5, as shown in FIG. 3. The indicator 100 is thus visible. After actuation, the pusher element 25 moves axially inside the skirt 5, as shown in FIG. 4. It is thus no longer visible from the outside, and the same applies for the indicator 100.

Advantageously, the indicator 100 may be formed by a colored strip that extends around said pusher element 25. Naturally, other embodiments are possible, in particular in relation to the shape and to the dimension/size of the indicator formed on the pusher element 25.

The present invention is described above with reference to an embodiment, but naturally any modification could be applied thereto by a person skilled in the art, without going beyond the ambit of the present invention, as defined by the accompanying claims.

The invention claimed is:

1. A dispenser device for dispensing a fluid or powder composition, the dispenser device comprising: a dispenser head that is provided with a dispenser outlet that is formed at the end of a hollow sleeve; an air expeller for generating a flow of air while the device is being actuated, said air expeller including a piston that slides in an air chamber between a rest position and a dispensing position, said air chamber including a cylindrical body in which said piston slides in airtight manner; and a reservoir that contains a single dose of composition, said reservoir including an air inlet that is connected to said air expeller, and a composition outlet that is connected to said dispenser outlet, said air inlet including a composition retainer member for retaining the composition in the reservoir until the composition is dispensed, and said composition outlet being closed by a closure element that is force fitted in the composition outlet of the reservoir; said device further comprising a mechanical opening system that co-operates with said closure element so as to expel it mechanically from its closed position while the device is being actuated; said device further comprising an indicator that, in the rest position before actuation, is in a first state, and that after actuation passes into a second state, the passage from the first to the second state informing the user that the device has been actuated, said device being characterized in that said first state is a visible state and said second state is a non-visible state, said device including a pusher element that is secured to said piston, and on which the user presses during actuation, said dispenser head including a skirt that is arranged around said air chamber, said pusher element, in its rest position before actuation, projecting axially out from said skirt, and after actuation, being arranged inside said skirt, said pusher element including an indicator that is visible before actuation and that is not visible after actuation.

2. A device according to claim 1, wherein said indicator is formed by a colored strip that extends around said pusher element.

* * * * *